United States Patent [19]

Turecek et al.

[11] Patent Number: 5,593,968
[45] Date of Patent: Jan. 14, 1997

[54] VIRUS-INACTIVATED FACTOR XA PREPARATION

[75] Inventors: Peter Turecek; Eibl Johann; Hans-Peter Schwarz, all of Vienna, Austria

[73] Assignee: Immuno Aktiengesellschaft, Vienna, Austria

[21] Appl. No.: 285,040

[22] Filed: Aug. 2, 1994

[30] Foreign Application Priority Data

Aug. 2, 1993 [DE] Germany .......................... 43 25 872.7

[51] Int. Cl.$^6$ .......................... A61K 38/36; A61K 35/16; C07K 14/745; C07K 1/16
[52] U.S. Cl. .............. 514/21; 435/68.1; 514/12; 514/834; 530/381; 530/382; 530/829; 530/830
[58] Field of Search ........................... 530/381, 382, 530/829, 830; 514/12, 21, 834; 435/68.1

[56] References Cited

U.S. PATENT DOCUMENTS

| | | | |
|---|---|---|---|
| 4,297,344 | 10/1981 | Schwinn et al. | 530/381 |
| 4,495,278 | 1/1985 | Thomas | 435/5 |
| 4,501,731 | 2/1985 | Tishkoff et al. | 424/530 |
| 4,640,834 | 2/1987 | Eibl et al. | 424/176.1 |
| 4,687,664 | 8/1987 | Philapitsch et al. | 435/236 |
| 5,410,022 | 4/1995 | Eibl et al. | 530/383 |

FOREIGN PATENT DOCUMENTS

| | | |
|---|---|---|
| 0129998 | 1/1985 | European Pat. Off. . |
| 0131740 | 1/1985 | European Pat. Off. . |
| 0159311 | 10/1985 | European Pat. Off. . |
| 0208215 | 1/1987 | European Pat. Off. . |
| 0214737 | 3/1987 | European Pat. Off. . |
| 0549964 | 7/1993 | European Pat. Off. . |
| 4325872 | 8/1994 | Germany . |
| 82/03871 | 11/1982 | WIPO . |

OTHER PUBLICATIONS

Radcliffe et al., "Comparisions of the Molecular Forms of Activated Bovine Factor X", J. Bio. Chem., 248(19):6788–6795 (1973).
Radcliffe et al., "The Purification and Properties of Activated Factor X", J. Bio. Chem., 247(23):7735–7742 (1972).
Yue et al., "Isolation of the High Molecular Form of Bovine Factor X and Some of its Physical Properties", Biochimica et Biophysica Acta 490:350–362 (1977).
Novoa et al., "Improved Procedures for the Purification of Selected Vitamin K–Dependent Proteins", Preparative Biology, 6(5):307–338 (1976).
J. C. Giddings, "Molecular Genetics and Immunoanalysis in Blood Coagulation", 1988, pp. 46–52.
Jesty et al., "The Activation of Cleavage Sites in the Alternative Pathays and Characterization of the Cooh–Terminal Peptide*", The Journal of Biological Chemistry, vol. 250, No. 12, Jun. 1975, pp. 4497–4504.
Jesty et al., "The Mechanism of Activation of Factor X", The Journal of Biological Chemistry, vol. 249, No. 17, Sep. 1974, pp. 5614–5622.
Fujikawa et al., "Activation of Bovine Factor X (Stuart Factor): Conversion of Factor $X_{a\alpha}$ to Factor $X_{a\beta}$", Proc. Nat. Acad. Sci., vol. 72, No. 9, Sep. 1975, pp. 3359–3363.
Teng et al., "Production of Factor X and Factor Xa Variants with Thrombin, Acutin and by Autolysis", Thrombosis Research, vol. 22, No. 1/2, 1981, pp. 213–220.
Bajaj et al., "Simultaneous Purification of Bovine Prothrombin and Factor", The Journal of Biological Chem., vol. 248, No. 22, Apr. 1973, pp. 7729–7741.
Mertens et al., "Pathways in the Activation of Human Coagulation Factor X", J. Biochem. vol. 185, 1980, pp. 647–658.
Wolf et al., "Design of Constructs for the Expression of Biologically Recombinant Human Factors X and Xa", J. Bio. Chem., vol. 266, No. 21, Jul. 1991, pp. 13726–13730.
H. G. J. Brummelhuis, "Preparation of the Prothrombin Complex", Acad. Pres, 1980, pp. 117–128.
Miletich et al., "The Synthesis of Sulfated Dextran Beads for Isolation of Human Plasma Coagulation Factors II, IX, and $X^1$", Analytical Biochem., 105, 1980, pp. 304–310.
Kisiel et al. "Factor X Activating Enzyme from Russell's Viper Venom: Isolation & Characterization" Biochemistry 15(22) 4901–4906 1976.

*Primary Examiner*—Mindy Fleisher
*Assistant Examiner*—Nancy J. Degen
*Attorney, Agent, or Firm*—Foley & Lardner

[57] ABSTRACT

A virus-inactivated Factor-Xa preparation with at least 100 units coagulation factor activity per mg protein is described, wherein this preparation is produced by activation of a corresponding starting material and subsequent treatment for the inactivation of infectious agents, particularly viruses. By incubation, the preparation obtained in this manner is transformed into a stable beta-Factor Xa preparation. In addition, the use of the present preparation for the treatment of hemophilia A inhibitor patients is disclosed.

32 Claims, No Drawings

VIRUS-INACTIVATED FACTOR XA PREPARATION

The invention relates to a virus-inactivated Factor Xa preparation, especially to a Factor Xa preparation of high purity. A method for the production of this virus-inactivated, highly pure Factor Xa preparation is described, wherein this method also allows especially a virus-inactivated, highly pure beta-Factor Xa preparation to be obtained which is distinguished by particular stability.

The blood coagulation Factor X represents a plasma glycoprotein which is involved in the intrinsic as well as the extrinsic blood coagulation cascade. During blood coagulation, Factor X is activated to Factor Xa. The latter represents a serine protease which catalyses the transformation of prothrombin to thrombin.

Factor X comprises two subunits, namely a heavy chain with a relative molar mass of 49 kD and a light chain with a relative molar mass of 17 kD which are connected by a disulfide bridge. Through the enzyme-catalysed activation of the zymogen to Factor Xa, an amino-terminal peptide with a relative molar mass of 11 kD is cleaved from the heavy chain. Through this, alpha-Factor Xa with a relative molar mass of approximately 55 kD results which represents the proteolytically active Factor Xa (J. C. Giddings, Molecular Genetics and Immunoanalysis in Blood Coagulation, Weinheim, Cambridge, N.Y., Basel, Verlag Chemie 1988, p. 47ff).

Beta-Factor Xa results through further cleavage of a 4.5 kD peptide from the carboxy-terminal end of the heavy chain of the alpha-Factor Xa. From the literature (J. Biol. Chem., 250: 4497–4504 (1975) and 249: 5614–5622 (1972)), it follows that this concerns an autocatalytic transformation of the alpha-Factor Xa into beta-Factor Xa (see also Proc. Nat. Acad. Sci. USA, 72: 3359–3363 (1975)). For this reason, commercially available Factor Xa preparations contain mixtures of alpha-Factor Xa and beta-Factor Xa. The commercially available Factor Xa preparations are largely produced through activation of Factor X with the aid of Russell's Viper Venom. It is known from J. Biol. Chem., 250: 4497–4504 (1975) that this enzymatic activation only leads to alpha-Factor Xa. A subsequent uncontrolled autocatalytic further transformation to beta-Factor Xa follows wherein mixtures of the both forms of Factor Xa result.

From the literature, it is known that alpha-Factor Xa and beta-Factor Xa possess the same enzymatic activities. However, for a pharmaceutical preparation, it is of essential importance that a Factor Xa product with molecular integrity of the active ingredient exists which also keeps through long-term storage excluding further transformations of Factor Xa.

From Thrombosis Research 22: 213–220 (1981), a method is known which permits the receipt of a rather stable beta-Factor Xa preparation. According to this method, beta-Factor Xa is stored cool in 50% glycerol at pH 7.2 in 0.03M imidazole buffer. Nevertheless, a further transformation to inactive fragments also appears through this method even when beta-Factor Xa is stored in the above-mentioned buffer at 4° C. In a similar manner, the instability of Factor Xa in glycerol-water mixtures is also described in J. Biol. Chem., 248: 7729–7741 (1973).

A method for the purification of Factor X from bovine plasma is known from J. Biol. Chem., 248: 7729–7741 (1973). This purification method comprises the adsorption of the Factor X to barium chloride, the elution of the same, and the subsequent fractionated purification with ammonium sulfate. A further purification is carried out chromatographically with anion exchangers. The purified Factor X is then activated through the effect of immobilised trypsin or RVV (Russell's Viper Venom).

The activation of purified human plasma Factor X is described in J. Biochem. 185, 647–658 (1980). As activators, RVV and/or purified physiological activators are employed. Factor VII, together with 'tissue factor', and Factor IXa/Factor VIII belong to the last group. As a result, the activated Factor X is obtained.

Plasma, for example, serves as starting material for the extraction of Factor X and/or Xa. Besides, Factor X and/or Xa can be recombinantly produced.

The use of biolological materials as starting materials and/or for the activation of Factor X harbors the risk of the existence of infectious agents in the preparation. Therefore, a treatment for the inactivation, especially of viruses, is absolutely required. The activated Factor Xa is also considered to be a labile enzyme (in comparison to the zymogen), for which reason it is preferred to treat the zymogen (Factor X) for virus inactivation. For safety reasons as well as reasons of stability it is suggested in U.S. Pat. No. 4,501,731 to administer the zymogen Factor X instead of Factor Xa for the treatment of blood coagulation disorders.

As already mentioned above, Factor X and/or the activated Factor Xa can also be obtained recombinantly. For example, the expression of Factor X and the activated form in transformed CHO-cells is described in J. Biol. Chem. 266, 13726–13730 (1991). The obtained coagulation Factors are purified by anion exchange and immunoaffinity chromatography. Although it concerns a mild method of preparation in this case, smaller specific activities in comparison to plasma Factor Xa were found. The comparison products concern plasma coagulation factors as they are commercially available from Hematologic Technologies. It is also known that recombinantly produced Factor Xa in its purified form is subject to autoproteolysis.

The object of the invention is to make available a virus-inactivated Factor Xa preparation of high purity. A further object according to the invention is to create a virus-inactivated, stable beta-Factor Xa preparation of high purity.

The present object is solved according to the invention by making available a virus-inactivated Factor Xa preparation with at least 100 units of coagulation Factor Xa activity per mg protein.

In addition, a virus-inactivated Factor Xa preparation with at least 100 units coagulation Factor beta-Xa activity per mg protein is made available.

Preferably, a virus-inactivated Factor Xa preparation with at least 500 and/or 1000 units per mg protein is made available. In addition, a stable, virus-inactivated beta-Factor Xa preparation with at least 100, preferably 500 and/or 1000, units of coagulation Factor Xa activity per mg is made available.

This is achieved by a new method in which a Factor X-containing starting material is, after activation to at least 100 units of Factor Xa activity per mg protein, purified and is subsequently subjected to a treatment for the inactivation of infectious agents, especially of viruses.

The present above-mentioned virus inactivation occurs preferably by a heat treatment. It is especially preferable to perform the heat treatment according to the method of EP-159,311, wherein the preparation to be inactivated in a solid state, as for example in lyophilized form, is adjusted to a content of water, methanol, or ethanol of more than 0.05 (corresponding to 5% by weight) and less than 0.70 (70% by weight) and is treated in a closed container at a temperature in the range from 50° to 121° C. under increase of the partial vapour pressure of the water, methanol or ethanol.

Preferably, the heat treatment for the virus inactivation occurs at a water content of 6 to 30% (w/w). Preferable temperatures for the heat treatment lie in the range from 50° to 90° C.

Surprisingly, it has been found according to the invention that, as opposed to the previously known opinion of the experts, the activated Factor X (Factor Xa) is sufficiently stable in a highly pure form so that it can be heat treated as well as stored over longer time without having to consider an essential loss of the biological activity. This effect was unexpected because proteins are all the more stabile, in general, when they are present together with accompanying proteins, especially carrier proteins. Thus, it is known in the art that, for example, albumin operates as such a carrier protein which causes a stabilization of, among others, blood factors.

It is known that highly purified Factor X (zymogen) is essentially more labile to heat treatment than a Factor X preparation which is present in the form of prothrombin complex, that is to say a fraction which comprises several proteins. Consequently, it was not expected that activated Factor X in highly purified form is sufficiently stable so that it can be heated for the virus inactivation without substantial denaturation.

As it is shown in the following Examples, the preparation according to the invention can be produced by chromatographic purification of a suitable starting material which contains Factor X, activation, and subsequent heat treatment, preferably in a solid state. The heat treatment can occur during 10 hours at 60° C. and 1 hour at 80° C. according to EP-159 311. In addition, it is possible to perform the heat treatment of the protein in aqueous solution, optionally after the addition of stabilizers.

According to a preferable execution according to the invention, Factor X is purified from a Factor X-containing fraction, optionally treated with a surfactant for the inactivation of lipid-enveloped viruses, and the purified Factor X is activated to Factor Xa by the effect of an enzyme; to this a further purification of Factor Xa as well as a heat treatment of the same is added. For this, either a plasma fraction, in particular a prothrombin complex, or a cell culture supernatant which contains the recombinant Factor X serves as starting material. In order to guarantee a maximal safety with respect to the transmission of infectious agents, it is adventageous to already treat the starting material, especially viruses, before the isolation of the Factor X for the inactivation of infectious agents. In this manner, the method of production comprises at least 2 measures for the inactivation of viruses.

Snake venom, especially RVV, in immobilized form or as a soluble enzyme can be used as an activating enzyme. In addition, also trypsin or a protease with trypsin-like activity or a physiological activator of intrinsic or extrinsic coagulation can be used. For example, an activated coagulation Factor, optionally with a co-factor, like Factor VIIa and tissue Factor, serves for this last group.

It is supposed that Factor Xa preparations are especially therapeutically valuable for the treatment of hemophilia when they are administered together with phospholipid preparations (for this, see EP-129 998). It is, however, known that the autocatalytic transformation of alpha-Factor Xa to beta-Factor Xa is augmented by lipids. A high stability of Factor Xa preparations is therefore above all desirable if they are administered together with phospholipid preparations.

It has been shown that the virus-inactivated, highly pure preparation according to the invention is excellently suitable for the treatment of hemophilia A inhibitor patients, above all when it is administered in combination with phospholipid preparations. This is especially due to the presence of the stable beta form.

Aside from the therapeutic use of the highly pure Factor Xa preparations according to the invention, these also find an advantageous use in diagnostics.

The invention is more closely described by the following examples.

EXAMPLE 1

Preparation of Factor X from a virus-inactivated plasma fraction by means of ion exchange chromatography.

A lyophilisate of a prothrombin complex factor preparation which contains the Factors II, IX, X as well as Protein C and Protein S was used as a starting material. This starting material was prepared according to the method of H. G. J. Brummelhuis (Preparation of the prothrombin complex; in Curling, J. M., Methods of Plasma Protein Fractionation, pages 117–128 (Acad. Press, New York, 1980)) and heat treated for virus inactivation according to EP-159,311.

Correspondingly, the lyophilisate (1000 U FX/g) was dissolved in distilled water so that the solution contains 50,000 U FX/l and was adjusted to pH 7.0. After the addition of 12% (V/V) Tween 80, the solution was stirred for 1 hour at room temperature. Subsequently the solution was diluted with distilled water to the 5-fold volume (corresponding to 10,000 U FX/l), mixed with trisodium-citrate-dihydrate (7 g/l), and adjusted to pH 7.0. By the addition of 80 ml 1M $BaCl_2$ solution per 10,000 U FX, the proteins of the prothrombin complex were co-precipitated The precipitate was sedimented by centrifugation (10 min, 4° C.) and washed three times with 1 l wash buffer per 10,000 U FX by resuspension and repeated centrifugation. (Wash buffer: For this a solution of 20 mM trisodium-citrate-dihydrate, 100 mM NaCl, 1 mM Benzamidine-HCl, and 10 mg/l soyabean-trypsin inhibitor, pH 6.0, was mixed with 80 ml 1M $BaCl_2$ solution per liter and the corresponding precipitate separated.)

The washed precipitate was resuspended with stirring at 4° C. for 30 minutes with 200 ml (per 10,000 U of FX used) of a 25% (W/V) ammonium sulphate solution which contained 50 mM benzamidine-HCl and subsequently centrifuged. The supernatant was separated and the pellet was again resuspended with ammonium sulphate solution and centrifuged again. The centrifugation supernatants were combined, brought to 80% saturation with ammonium sulphate and stirred at 4° C. for 15 hours. The ensuing precipitate from this was obtained by centrifugation. The pellet was suspended in buffer (25 mM trisodium-citrate-dihydrate, 100 mM NaCl, 1 mM benzamidine-HCl, pH 6.0) at a concentration of 50,000 U FX/l, chromatographed with the same buffer over a Sephadex® G25 column, and the fractions were collected. While doing so, the UV-absorption at 280 nm and the electric conductivity of the eluate was measured. The protein containing fractions were combined and adjusted to 40,000 U FX/l.

Subsequently, the prothrombin complex Factors were separated by chromatography on DEAE-Sepharose-Fast-Flow®. In addition, 10 U FX/ml of gel were adsorbed to a column (inner diameter: gel bed height=1:8,3), with swelled, washed DEAE-Sepharose gel at a flow rate of 2 ml/min. Thereafter, the column was washed with a flow rate of 2 ml/min with the 1.7-fold gel volume of 100 mM NaCl in 25 mM trisodium-citrate-dihydrate, pH 6.0, and subsequently with the 2.6-fold gel volume of 250 mM NaCl in 25 mM citrate buffer, pH 6.0. The elution of FX occurred with the 5.2-fold gel volume of 280 mM NaCl in citrate buffer, pH 6.0 (protein still bound to the gel was removed with 1M NaCl in buffer and by washing with a base).

Through the elution, fractions were collected which were analyzed for the content of FX, Protein C, FIX and FII. The FX-containing fractions which were free from FII and poor in FIX and Protein C were combined, brought to 80% saturation with ammonium sulphate, and stirred for 15 hours at 4° C. The resulting precipitate was separated by centrifugation and dissolved in 20 mM Tris-HCl buffer, pH 7.4 which contained 50 mM NaCl and 2 mM $CaCl_2$ (TBSC buffer), rebuffered by chromatography against 20 mM TBSC buffer over a column filled with Sephadex® G25, and adjusted to 3 U FX/ml.

The entire contents of EP 159 311 is refered to concerning the method conditions for the heat treatment. This European patent should be a part of the present description.

EXAMPLE 2

Alternative Method for the Production of Factor X

The lyophilisate of a prothrombin-complex factors preparation was dissolved as described in Example 1 and treated with Tween 80. After dilution to 10,000 U FX/l, it was mixed with 30 g/l $Ca_3(PO_4)_2$ and stirred for 1 h at room temperature. Thereafter, the solid phase was separated by centrifugation, washed by resuspension two times each with 25 ml/g calcium phosphate of a buffer of 20 mM Tris-HCl, pH 7.0, containing 10% ammonium sulfate, and in each case centrifuged again. Thereafter, a third washing by repeated resuspension with 25 ml/g calcium phosphate of a buffer of 20 mM Tris-HCl, pH 7.0, containing 150 mM NaCl, and subsequent centrifugation was carried out.

For the elution of the adsorbed Factor X, the pellet was stirred with 1M sodium phosphate buffer, pH 7.0 (25 ml elution solution/g calcium phosphate used) for 1 h at room temperature. Thereafter, the solid phase was separated by centrifugation and the Factor X-containing supernatent was brought to 80% saturation with ammonium sulfate and stirred for 15 h at 4° C. The ensuing precipitate was obtained in this way by centrifugation. As described in Example 1, paragraph 4, the pellet was rebuffered over Sephadex® G25 and subsequently conveyed to DEAE-Sepharose-Fast-Flow® for chromatography.

EXAMPLE 3

Production of Factor X from a virus-inactivated plasma fraction with the aid of ion exchange and affinity chromatography.

The Factor X-containing solution produced according to Example 1 or 2 was further purified over a dextran sulphate gel according to the method of J. P. Milerich et al (Analytical Biochemistry, 105, 304–310 (1980)). The FX-containing fraction obtained in this manner was brought to 80% saturation with ammonium sulphate and stirred for 15 h at 4° C. The obtained precipitate was separated by centrifugation, dissolved in 20 mM Tris-HCl buffer containing 150 mM NaCl and 2 mM $CaCl_2$, pH 7.4 (TBSC buffer), rebuffered by chromatography against 20 mM TBSC buffer over a column filled with Sephadex® G25, and adjusted to 3 U FX/ml.

EXAMPLE 4

Quantitative measurement of Factor Xa

Test principle:

The chromogenic peptide substrate $CH_3OCO$-D-CHA-Gly-Arg-pNA is hydrolized by Factor Xa whereby $CH_3OCO$-D-CHA-Gly-Arg-OH and paranitroaniline is obtained. The kinetics of the increase of paranitroaniline is measured spectrophotometrically at 405 nm. The increase of the optical density (O.D.) is proportional to the content of Factor Xa in the sample to be quantitated.

Reagents:

Dilution buffer:

3.7 g/l Tris-(hydroxymethyl)-aminomethane 2.1 g/l Imidazol 18.0 g/l NaCl 1.0 g/l Human albumin pH 8.4

Substrate solution:

1.3 mM $CH3OCO$-D-CHA-Gly-Arg-pNA in dilution buffer

Methods:

50 μl of a sample containing Factor Xa are mixed with 50 μl of dilution buffer and incubated for 90 seconds at 37° C. Then 100 μl of the substrate solution are added and the increase of the O.D. per minute at 37° C. at 405 nm is measured. The increase of the O.D. must stay linearly constant during the time period of measurement.

For the drawing of a reference curve, the standard preparation of bovine Factor Xa "NIBSC-Reagent 75/595" is used, wherein an ampule contains 1 U FXa after reconstitution with 1 ml destilled water (see data sheet, National Institute for Biological Standards and Controls).

EXAMPLE 5

Production of beta-Factor Xa from Factor X

The FX solution produced according to Examples 1, 2, or 3 was mixed with 0.14 mg RVV (FX-activating protease from Vipera russellii) per 100 U FX and stirred for 1 h at room temperature. Thereafter, the incubation mixture was adsorbed at a flow rate of 3 ml/min to benzamidine-Sepharose® (washed and swelled), packed in a column (inner cross-section: gel bed height=1:3) corresponding to 5 E FX/ml gel. For the removal of inert proteins this was washed with the 3.5-fold gel volume at the same flow with TBSC buffer. Factor Xa was eluted with 30 mM benzamidine-HCl in TBSC buffer and collected in fractions. The alpha- and beta-FXa containing fractions were combined, mixed with ammonium sulphate (80% saturation), and stirred for 15 h at 4° C. The obtained precipitate was separated from the supernatant by centrifugation at 4° C. and dissolved in 20 mM Tris-HCl buffer containing 150 mM NaCl, pH 7.4 (TBS).

For the quantitative transformation of the FXa into pure beta-FXa the above obtained solution was incubated for 3 h at 37° C. After that, it was rebuffered against TBS over Sephadex® G25, sterile filtered (0.22 μm filter) and subseqently adjusted to 200 U beta-FXa/ml (in this way, the preparation is present in TBS).

A beta-FXa preparation prepared according to this method has a specific activity of 2,550 U FXa/mg protein.

Variant A

A beta-FXa solution produced according to Example 5 was mixed with saccharose so that the final preparation contained 5 g/100 ml.

This specific activity was as described above.

Variant B

A beta-FXa solution produced according to variant A was mixed with 1 g/100 ml human albumin (HUMAN ALBUMIN 20% IMMUNO, heat treated).

A beta-FXa preparation prepared according to this method has a specific activity of at least 20 U FXa/mg protein (before the albumin addition this specific activity amounted to 2550 U/mg protein).

EXAMPLE 6

Lyophilization of Factor Xa

A beta-FXa preparation produced according to Example 5 was shock-frozen and lyophilized.

After reconstitution of the lyophilizate in the original volume, more than 50% of the starting activity of FXa could be determined in all cases.

EXAMPLE 7

Heat treatment of lyophilized beta-Factor Xa

For the inactivation of potentially present pathogens, the lyophilized beta-FXa preparations of Example 6 were heated under increase of the partial water vapour pressure according to the described methods in patent EP-159 311 or were treated in the same way following the treatment at 60° C. for a further 1 hour at 80° C. The yield of FXa amounted to more than 90% in every case.

EXAMPLE 8

Thermostability of Factor X in a prothrombin complex preparation in comparison to highly purified Factor X The following experiments provide a comparison of the stability with respect to the heat denaturation of differently pure preparations of Factor X. While it was known to the expert that the zymogen of Factor X is essentially more stable than the activated Factor Xa, it has surprisingly been shown according to the invention that, nevertheless, this activated Factor Xa can be subjected to a heat treatment without an appreciable loss of the biological activity. This was not predictable in the art.

The following experiments were carried out for a stability comparison of differently pure Factor X preparations: A prothrombin-complex Factors preparation was prepared according to the method of H. G. J. Brummelhuis (Preparation of the prothrombin complex; in Curling, J. M., Methods of Plasma Protein Fractionation, pages 117–128 (Acad. Press, New York, 1980)) and heat treated for the virus inactivation according to the method according to EP-159 311. This specific activity of Factor X in this preparation amounted to 1.36 U/mg protein. Moreover, Factor II showed a specific activity of 1.33 U/mg protein and Factor IX showed a specific activity of 1.12 U/mg protein.

In a further experiment, Factor X was produced as in Example 1, however, after ensuing ammonium sulphate precipitation, it was rebuffered against a buffer consisting of 6 g/l trisodium-citrat and 7 g/l NaCl, pH 7.35, by chromatography on Sephadex® G25. This specific activity of this Factor X preparation amounted to 45 U/mg protein.

Both Factor X preparations were diluted to 7 U FX/ml in the above-mentioned buffer and lyophilized. Subsequently, they were moistened to 7.5% (w/w) of water and in each case heated either for 1 hour at 95° C., 2 hours at 95° C. or 10 hours at 60° C. Thereafter, the Factor X content of the samples was measured and the decrease in activity was ascertained in comparison to the not-heated Factor X (see Table 1). By this, it was shown that highly pure Factor X had a decrease in activity of an average of 20% by the thermal treatment, while the activity of Factor X in the prothrombin complex remained essentially unchanged.

TABLE 1

| Treatment | FX % Residual activity | |
|---|---|---|
| | FX pure | FX in PPK |
| not heated | 100 | 100 |
| 1 h/95° C. | 81 | 99.6 |
| 2 h/95° C. | 78.5 | 94.5 |
| 10 h/60° C. | 82 | 100 |

Therefore, because the highly purified zymogen of Factor X is less stable in a heat treatment than the above-mentioned comparison substance, the expert would have expected that an essentially higher loss of the biological activity in an identical treatment of highly pure activated Factor Xa occurs. However, surprisingly this is not the case in the method according to the invention.

EXAMPLE 9

Storage stability of beta-Factor Xa

A preparation of beta-Factor Xa was produced according to Example 5 and a volume of 1 ml each was lyophilized for every 1 ml at a dilution of 2.8 U/ml. The lyophilizates were stored at 37° C. over 6 weeks, wherein a sample was taken once per week and was examined for its content of Factor Xa as described in Example 4. No change of the activity of beta-Factor Xa during the storage time period resulted.

We claim:

1. A method for the production of a virus-safe Factor Xa pharmaceutical preparation, comprising the steps of:

obtaining a human Factor Xa preparation having an activity of at least 100 units of Factor Xa activity per mg protein; and treating said human Factor Xa preparation to inactivate viruses while substantially avoiding denaturation of Factor Xa in order to obtain said virus-safe Factor Xa pharmaceutical preparation.

2. A method according to claim 1, wherein said Factor Xa preparation is obtained by activation of Factor X.

3. A method according to claim 2, wherein said Factor X is from a source selected from the group consisting of plasma, a prothrombin complex and recombinant cells.

4. A method according to claim 2, wherein said Factor X is purified from said source by chromatography.

5. A method according to claim 2, wherein said activation employs Russell's Viper Venom or a protease with a trypsin-like activity.

6. A method according to claim 2, wherein said activation employs an activated coagulation factor.

7. A method according to claim 2, wherein said activation employs Factor VIIa and tissue factor.

8. A method according to claim 1, wherein said Factor Xa preparation has at least 500 units of Factor Xa activity per mg protein.

9. A method according to claim 8, wherein said Factor Xa preparation has at least 1000 units of Factor Xa activity per mg protein.

10. A method according to claim 1, wherein said treating step employs heat.

11. A method according to claim 1, wherein said treating step is carried out by heating at a temperature of 50° C.

12. A method according to claim 1, wherein during said treating step said Factor Xa preparation is heated in a solid state with a water content of 6–30% (w/w).

13. Virus-safe human Factor Xa pharmaceutical preparation with at least 100 units coagulation Factor beta-Xa activity per mg protein and substantially without denaturation products.

14. A pharmaceutical preparation according to claim 2 with at least 500 units coagulation Factor beta-Xa activity per mg protein.

15. A pharmaceutical preparation according to claim 2 with at least 1,000 units coagulation Factor beta-Xa activity per mg protein.

16. A method for the production of a virus-safe preparation containing beta-Factor Xa, comprising the steps of:

obtaining a human alpha-Factor Xa preparation having an activity of at least 100 units of Factor Xa activity per mg protein;

transforming human alpha-Factor Xa to beta-Factor Xa; and treating said beta-Factor Xa to inactivate viruses while substantially avoiding denaturation of Factor Xa in order to obtain said virus-safe preparation containing beta-Factor Xa.

17. A method according to claim 16, wherein said alpha-Factor Xa preparation is obtained by activation of Factor X.

18. A method according to claim 16, wherein said alpha-Factor Xa preparation has at least 500 units of Factor Xa activity per mg protein.

19. A method according to claim 16, wherein said alpha-Factor Xa preparation has at least 1000 units of Factor Xa activity per mg protein.

20. A method according to claim 16, wherein said treating step employs heat.

21. A method according to claim 20, wherein said treating step is carried out by heating at a temperature of 50°–90° C.

22. A method according to claim 21, wherein during said treating step said beta-Factor Xa preparation is heated in a solid state with a water content of 6–30% (w/w).

23. A method according to claim 16, wherein said transforming step comprises incubating said alpha-Factor Xa preparation at a temperature of 4°–40° C. for 1–24 hours.

24. A method according to claim 23 wherein said transforming step comprises incubating said alpha-Factor Xa preparation at a temperature of 17°–37° C. for 2–4 hours.

25. A method according to claim 16, wherein said treating step is undertaken before said transforming step.

26. A method according to claim 16, wherein said treating step is undertaken after said transforming step.

27. A method of treating Hemophilia A inhibitor patients, comprising the step of administering to said patient a virus-safe preparation containing beta-Factor Xa obtainable by a method comprising the steps of:

obtaining a human alpha-Factor Xa preparation having an activity of at least 100 units of Factor Xa activity per mg protein;

transforming human alpha-Factor Xa to beta-Factor Xa; and treating said beta-Factor Xa to inactivate viruses while substantially avoiding denaturation of Factor Xa in order to obtain said virus-safe preparation containing beta-Factor Xa.

28. A virus-safe Factor Xa preparation, wherein the Factor Xa has been quantitatively transformed to the beta form.

29. A method of treating patients with blood coagulation disorders, comprising the step of administering to said patient a virus-safe pharmaceutical preparation containing Factor Xa in the beta form.

30. A method according to claim 29, wherein said virus-safe Factor pharmaceutical preparation has at least 100 units coagulation Factor beta-Xa activity per mg protein.

31. A method according to claim 30 wherein said patient is a hemophiliac.

32. A method according to claim 30, wherein said patient has an inhibitor disorder.

* * * * *

UNITED STATES PATENT AND TRADEMARK OFFICE
CERTIFICATE OF CORRECTION

PATENT NO. : 5,593,968
DATED : January 14, 1997
INVENTOR(S) : Peter TURECEK et al.

It is certified that error appears in the above-identified patent and that said Letters Patent is hereby corrected as shown below:

On title page, insert the following between "[73] Assignee: Immuno Aktiengesellschaft, Vienna, Austria" and "[21] Appl. No. 285,040" the following: --[*] Notice: The term of this patent shall not extend beyond the expiration date of Pat. No. 5,639,730.--

Signed and Sealed this

Twenty-fourth Day of March, 1998

Attest:

BRUCE LEHMAN

*Attesting Officer*       *Commissioner of Patents and Trademarks*